United States Patent [19]
Komer

[11] Patent Number: 5,773,422
[45] Date of Patent: Jun. 30, 1998

[54] AVERMECTIN FORMULATION

[76] Inventor: Gene Komer, 2817 W. County Rd. 54G, Fort Collins, Colo. 80524

[21] Appl. No.: 593,075

[22] Filed: Jan. 29, 1996

[51] Int. Cl.$^6$ .................................................. A61K 31/70
[52] U.S. Cl. ............................................................. 514/30
[58] Field of Search ........................ 514/30, 7.1; 536/7.1

[56] References Cited

U.S. PATENT DOCUMENTS

| | | | |
|---|---|---|---|
| 4,772,460 | 9/1988 | Malook et al. ............................ | 424/10 |
| 4,853,372 | 8/1989 | Williams et al. ......................... | 514/30 |
| 4,912,090 | 3/1990 | Yanai et al. .............................. | 514/30 |
| 4,916,120 | 4/1990 | Roben et al. ............................. | 514/30 |

FOREIGN PATENT DOCUMENTS

WO94/27611  8/1994  WIPO ............................ A61K 31/65

OTHER PUBLICATIONS

*Analytical Profiles of Drug Substances*; vol. 17, pp. 156–184; "Ivermectin" by David W. Fink (1988).

*Primary Examiner*—Elli Peselev
*Attorney, Agent, or Firm*—Greenlee, Winner and Sullivan, P.C.

[57] ABSTRACT

Novel formulations are disclosed for the administration of an avermectin, based upon the use of N-methylpyrrolidone or 2-pyrrolidone or mixtures thereof to dissolve avermectin. Formulations can contain from 0.1 to 40% by weight dissolved in at least 5% by volume of N-methylpyrrolidone, 2-pyrrolidone or mixture thereof. Various formulations are suitable for administration by intramuscular or subcutaneous injection, by topical application, stomach intubation, oral and drench administration.

26 Claims, No Drawings

AVERMECTIN FORMULATION

FIELD OF THE INVENTION

The invention relates to novel formulations for the administration of therapeutic doses of avermectins generally and ivermectin in particular.

BACKGROUND OF THE INVENTION

The avermectins are a family of closely related compounds produced by *Streptomyces avermitilis* or by synthetic or semi-synthetic means. A representative structure is shown for ivermectin which is semi-synthetic derivative: 22,23-dihydroavermectin $B_1$, containing at least 80% 22,23-dihydroavermectin $B_{1a}$ and not more than 20% 22,23-dihydroavermectin $B_{1b}$:

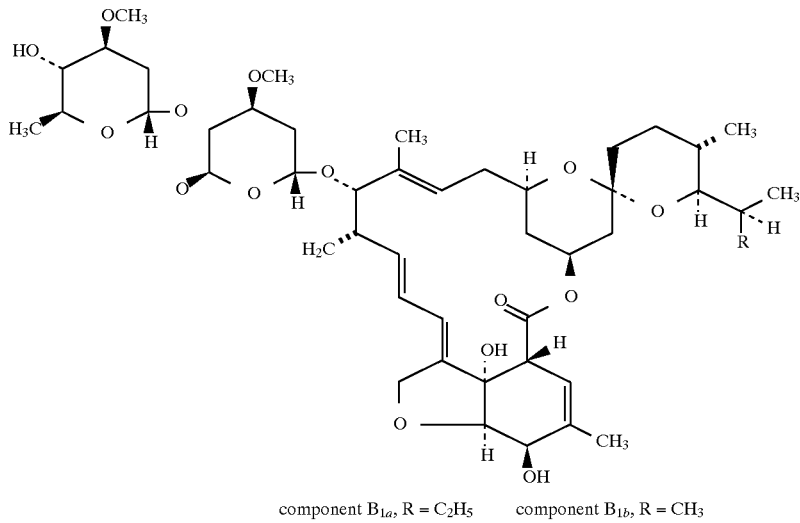

component $B_{1a}$, R = $C_2H_5$    component $B_{1b}$, R = $CH_3$

Members of the avermectin (C-076) family include other derivatives of pentacyclic 16-membered lactones, primarily $A_{1a}$, $A_{2a}$, $B_{1a}$, $B_{2a}$ as well as minor components $A_{1b}$, $A_{2b}$, $B_{1b}$, $B_{2b}$, all of which share to some degree activity as antiparasitics and antiagaricidics. Ivermectin has been marketed for treatment of various helminth intestinal parasites and heartworm in animals and for onchocerciasis (river blindness) in humans. The broad spectrum of activity of the avermectins make them attractive candidates for treatment of a variety of endo- and ectoparasites.

Ivermectin is described in U.S. Pat. No. 4,199,569. In common with other avermectins, ivermectin is poorly soluble in water, about 0.005 mg per ml at room temperature. Solubility in organic solvents varies, depending upon solvent, without clear trends. As reported by Fink, D. W. in *Analytical Profiles of Drug Substances*, Vol. 17:156–184, Academic Press, New York (1988), solubility in 1-butanol is 330 mg/ml but in 2-propanol is only 70 mg/ml. For ketone solvents, solubility in methylethylketone is 320 mg/ml but in acetone is only 81 mg/ml. Avermectin solubility in N-methylpyrrolidone has not been reported.

Two types of formulations for parenteral administration of ivermectin have been described. An aqueous micelle formulation is described in U.S. Pat. No. 4,389,397. A soluble formulation is disclosed in U.S. Pat. No. 4,853,372. The latter uses a solvent mixture of glycerol formal and propylene glycol (from 10:90 to 90:10) or of propylene glycol and water (from 95:5 to 80:20). The soluble formulations were said to be more effective against ectoparasites, such as ticks. Concentrations of from 0.1% to 20% by weight of ivermectin in the formulations were reported.

The use of N-methylpyrrolidone as a solvent for parenteral administration of oxytetracycline was disclosed in U.S. Pat. No. 4,772,460 and in International Publication WO 94/27611. N-methylpyrrolidone was found to be more suitable as an injectable solvent than 2-pyrrolidone.

SUMMARY OF THE INVENTION

It has been unexpectedly found that avermectins are sufficiently soluble in N-methylpyrrolidone or 2-pyrrolidone and mixtures of the two, to permit them to be used as suitable solvents for ivermectin formulations for intramuscular injection, subcutaneous injection, topical pour-on, stomach intubation, oral and drench administration. Formulations of avermectins are disclosed herein, including N-methylpyrrolidone as solvent, together with stabilizers, extenders, surfactants, preservatives and the like for various treatment and dosage regimens, as understood in the art. Various formulations described herein using ivermectin can be made using any of the avermectins since the latter differ only slightly from one another in chemical structure.

Formulations of the invention including N-methylpyrrolidone, or 2-pyrrolidone and mixtures thereof, have the advantages of providing higher concentrations of avermectin, allowing smaller dose quantities to be delivered, having improved stability and extended shelf life, increased concentrations of avermectin in the bloodstream and other extracellular fluid compartments and less pain, swelling and tissue damage at the injection site compared to currently available formulations. N-methylpyrrolidone and 2-pyrrolidone can also be used for transdermal absorption applications such as pour-on formulations and transdermal patches. Formulations of the invention including N-methylpyrrolidone and/or 2-pyrrolidone can be designed to provide therapeutic levels of avermectin over a sufficient period of time to be more effective against ectoparasites.

DETAILED DESCRIPTION OF THE INVENTION

As noted, ivermectin has unexpectedly been found to be sufficiently soluble in N-methylpyrrolidone as well as 2-pyrrolidone to permit formulation of various therapeutic compositions. Both N-methylpyrrolidone and 2-pyrrolidone have been approved as a safe solvent for injection, but only for oxytetracycline; which is chemically unlike ivermectin. N-methylpyrrolidone is preferred for injection formulations since it causes less pain at the injection site and less tissue reaction than does 2-pyrrolidone. Ivermectin can be present in the formulation from 0.1% to 40% (w/v). N-methylpyrrolidone (also known as M-pyrole) can be present from 5% to essentially 100% (v/v) of the formulation. The specific gravity of N-methylpyrrolidone is 1.027 at 25° C. relative to water at 4° C. Additional compounds can be included as desired, e.g. propylene glycol up to 95% by volume, water up to 90% by volume and Clorsulon (an antiparasitic agent frequently co-administered with ivermectin) up to 40% by weight. The formulation can contain water up to amounts which limit avermectin solubility. The maximum amount of water which can be included depends upon the amount of avermectin and the presence of co-solvents such as propylene glycol, and presence of detergent, as illustrated in the Examples. The amount of water which can be present is limited only by avermectin solubility. The presence of too much water can be readily detected because the clear solution becomes milky or cloudy as excess water is added. Where N-methylpyrrolidone is the sole solvent, up to 30% by volume of water can be included in a formulation containing 1% (w/v) ivermectin. If less ivermectin is present, the amount of water can be increased somewhat. If 10% (v/v) propylene glycol is a co-solvent with 20% (w/v) N-methylpyrrolidone, 0.5% ivermectin remains soluble in the presence of water up to about 70% by volume. Compositions containing 2-pyrrolidone completely or partially substituted for N-methylpyrrolidone in the exemplified formulations are equivalent in their solubility properties. As noted above, compositions containing N-methylpyrrolidone are preferred.

The formulations are readily prepared by dissolving ivermectin (a white crystalline powder) or other avermectin compound or mixture thereof, in N-methylpyrrolidone and/or 2-pyrrolidone, then adding remaining components of the desired formulation to achieve the final desired concentration of the drug and final ratios of other compounds. Where a co-solvent is used, such as propylene glycol, the avermectin can be dissolved in as much co-solvent or N-methylpyrrolidone/co-solvent mixture as needed to dissolve the drug.

Sterilization of the formulation can be carried out by membrane filtration, provided the membrane filter material is itself insoluble in and compatible with the formulation.

A phenomenon encountered with parenteral administration of a water-insoluble drug is that the drug can precipitate at the injection site (subcutaneous or intramuscular) from which it becomes released slowly over a period of time. The phenomenon can be turned to advantage provided the amount deposited and rate of release combine to provide therapeutically effective drug levels without excessive swelling at the site of injection or tissue damage. For ivermectin formulations, control of ectoparasites requires therapeutic drug levels over a longer treatment period than for control of endoparasites. Certain formulations of the invention are advantageous for ectoparasite control in that they allow injection of a higher drug concentration than previous formulations, permitting deposition of therapeutically effective amounts of the drug in a smaller injection volume than heretofore. In addition, the formulations of the invention are compatible with in situ solubilizing agents such as polyvinylpyrrolidone or polyethylene glycol and with surfactants such as polysorbate 80. Such components provide more rapid absorption of the drug after intramuscular or subcutaneous injection. The use of such components improves safety for intramuscular injection. Since the N-methylpyrrolidone solvent is essentially an inert, aprotic solvent, the formulations are highly stable and the opportunity for activity loss due to reaction of avermectin with the solvent is minimized. The N-methylpyrrolidone-propylene glycol vehicle is further advantageous in being compatible with most antimicrobial preservatives such as benzyl alcohol and methyl-, ethyl- and propylparaben. A desired goal in the veterinary field is to provide a multiple-dose injection product that retains sterility with multiple uses. The ability to combine the avermectin with an antimicrobial preservative of low aqueous solubility, such as methylparaben, can provide sustained antimicrobial activity not only within the dispenser but also within the injection site. As a further advantage, N-methylpyrrolidone is able to promote transdermal absorption of avermectins. Formulations are therefore provided for topical transdermal patch and pour-on applications for both ecto- and endoparasite control. Formulations of the invention are also suitable for stomach intubation, oral and drench administration. N-methylpyrrolidone is known to have a very low order of oral toxicity (Rat $LD_{50}$ 4200 mg/kg). Most of the compound is eliminated by the kidneys within 24 hours.

The following formulations are provided by way of exemplary embodiments of the invention. 2-Pyrrolidone can be substituted for all or part of the N-methylpyrrolidone in the following formulations:

GENERAL FORMULATIONS

Example 1 (Ivermectin Injection)

Ivermectin: 0.10% w/v to 40% w/v
N-methylpyrrolidone: 5% v/v to 100% v/v
Propylene Glycol: 90% v/v to 0% v/v
Water: 30% v/v to 0% v/v Example 2 (Ivermectin-F Injection)

Ivermectin: 0.10% w/v to 40% w/v
Clorsulon: 0.10% w/v to 40% w/v
N-methylpyrrolidone: 5% v/v to 100% v/v
Propylene Glycol: 90% v/v to 0% v/v
Water: 30% v/v to 0% v/v Example 3

Ivermectin: 1% w/v (10 mg/mL)
N-methylpyrrolidone: 100% v/v

Example 4

Ivermectin: 1% w/v (10 mg/mL)
N-methylpyrrolidone: 70% v/v
Water: q.s. 30% v/v

Example 5

Ivermectin: 1% w/v (10 mg/mL)
Clorsulon: 10% w/v (100 mg/mL)
N-methylpyrrolidone: 30% v/v
Propylene Glycol: q.s. 70% v/v Example 6

Ivermectin: 1% w/v (10 mg/mL)
Clorsulon: 10% w/v (100 mg/mL)

N-methylpyrrolidone: q.s. approx. 100% v/v

Example 7 (Subcutaneous Injection)

Ivermectin: 10 mg/mL
N-methylpyrrolidone: 30% v/v
Propylene Glycol: q.s

Example 8 (Subcutaneous Injection)

Ivermectin: 10 mg/mL
Clorsulon: 100 mg/mL
N-methylpyrrolidone: 30% v/v
Propylene Glycol: q.s.

Example 9 (Subcutaneous Injection)

Ivermectin: 0.27% w/v
N-methylpyrrolidone: 40% v/v
Water for Injection: 10% v/v
Propylene Glycol: q.s.

Example 10 (Subcutaneous Injection)

Ivermectin: 10 mg/mL
N-methylpyrrolidone: 30% v/v
Benzyl Alcohol: 1.5% v/v
Water for Injection: 10% v/v
Propylene Glycol: q.s.

Example 11 (Intramuscular Injection)

Ivermectin: 10 mg/mL
N-methylpyrrolidone: 30% v/v
Polyvinylpyrrolidone: 20% w/v
Methylparaben: 0.18% w/v
Propylparaben: 0.02% w/v
Propylene Glycol: q.s.

Example 12 (Intramuscular Injection)

Ivermectin: 20 mg/mL
N-methylpyrrolidone: 40% v/v
Polyethylene Glycol: 30% w/v
Propylene Glycol: q.s.

Example 13 (Intramuscular Injection)

Ivermectin: 10 mg/mL
N-methylpyrrolidone: 30% v/v
Polyvinylpyrrolidone: 20% w/v
Benzyl Alcohol: 1.5% v/v
Propylene Glycol: q.s.

Example 14 (Intramuscular Injection)

Ivermectin: 10 mg/mL
N-methylpyrrolidone: 30% v/v
Polysorbate 80: 10% v/v
Polyoxyethylene fatty acid ester: 10% v/v
Benzyl Alcohol: 1.5% v/v
Propylene Glycol: q.s.

Example 15 (Pour-on Formulation)

Ivermectin: 5 mg/mL
N-methylpyrrolidone: 20% v/v
Propylene Glycol: 10% v/v
FD&C Blue #1: 0.01 mg/mL
Purified Water: q.s.

Example 16 (Pour-on Formulation)

Ivermectin: 5 mg/mL
N-methylpyrrolidone: 10% v/v
Polysorbate 80: 5% v/v
FD&C Blue #1: 0.01 mg/mL
Benzyl Alcohol: 1.5% v/v
Purified Water: q.s.

Example 17 (Stomach Intubation, Oral and Drench Formulation)

Ivermectin: 10 mg/mL
N-methylpyrrolidone: 5% v/v
Propylene Glycol: 20% v/v
Polysorbate 80: 10% v/v
Benzyl Alcohol: 1.5% v/v
Purified Water: q.s.

Example 18 (Stomach Intubation, Oral and Drench Formulation)

Ivermectin: 10 mg/mL
N-methylpyrrolidone: 20% v/v
Propylene Glycol: 20% v/v
Benzyl Alcohol: 1.5% v/v
Purified Water: q.s.

I claim:

1. An injectable formulation for administering an avermectin comprising from 0.1% to 40% by weight of an avermectin dissolved in a solvent comprising at least 5% by volume N-methylpyrrolidone, or 2-pyrrolidone, or a mixture thereof.

2. The formulation of claim 1 wherein the avermectin is ivermectin.

3. The formulation of claim 2 wherein the solvent is a mixture of N-methylpyrrolidone, or 2-pyrrolidone, or a mixture thereof, and propylene glycol.

4. The formulation of claim 3 further comprising up to 20% by weight polyvinylpyrrolidone.

5. The formulation of claim 2 comprising at least 10% N-methylpyrrolidone, or 2-pyrrolidone, or a mixture thereof, and further comprising up to 30% by volume water.

6. The formulation of claim 3 comprising at least 10% by volume propylene glycol, and further comprising water.

7. The formulation of claim 2 further comprising a surfactant.

8. The formulation of claim 2 further comprising a preservative.

9. The formulation of claim 2 further comprising Clorsulon.

10. The formulation of claim 2 further comprising polyethylene glycol up to 30% by weight.

11. A formulation according to claim 1 further comprising a maximum of 90% by volume propylene glycol.

12. A formulation according to claim 11 further comprising from 0.10% to 40% by weight Clorsulon.

13. A formulation according to claim 2 consisting essentially of 1% by weight ivermectin dissolved in N-methylpyrrolidone.

14. A formulation according to claim 2 consisting essentially of 1% by weight ivermectin, 70% by volume N-methylpyrrolidone, and water.

15. A formulation according to claim 6 comprising 1% by weight ivermectin, 10% by weight Clorsulon, and N-methylpyrrolidone.

16. A formulation according to claim 15 wherein the N-methylpyrrolidone is 30% by volume, the formulation further comprising propylene glycol.

17. A formulation according to claim 3 wherein the ivermectin is 10 mg/ml and the N-methylpyrrolidone is 30% by volume.

18. A formulation according to claim 17 comprising additionally 100 mg/ml Clorsulon.

19. A formulation according to claim 3 wherein ivermectin is 0.27% by weight, N-methylpyrrolidone is 40% by volume, the formulation further comprising 10% by volume water.

20. A formulation according to claim 3 wherein ivermectin is 10 mg/ml, N-methylpyrrolidone is 30% by volume, the formulation further comprising 1.5% by volume benzyl alcohol and 10% by volume water.

21. A formulation according to claim 3 wherein ivermectin is 10 mg/ml, N-methylpyrrolidone is 30% by volume, the formulation further comprising 20% by weight polyvinylpyrrolidone, 0.18% by weight methylparaben, and 0.02% by weight propylparaben.

22. A formulation according to claim 3 wherein ivermectin is 20 mg/ml, N-methylpyrrolidone is 40% by volume, the formulation further comprising 30% by weight polyethylene glycol.

23. A formulation according to claim 3 wherein ivermectin is 10 mg/ml, N-methylpyrrolidone is 30% by volume, the formulation further comprising 20% by weight polyvinylpyrrolidone and 1.5% by volume benzyl alcohol.

24. A formulation according to claim 3 wherein ivermectin is 10 mg/ml, N-methylpyrrolidone is 30% by volume, the formulation further comprising 10% by volume polysorbate 80, 10% by volume polyoxyethylene fatty acid ester and 1.5% by volume benzyl alcohol.

25. A formulation according to claim 3 wherein ivermectin is 10 mg/ml, N-methylpyrrolidone is 5% by volume, propylene glycol is 20% by volume, the formulation further comprising polysorbate 80 10% by volume, benzyl alcohol 1.5% by volume, and water.

26. A formulation according to claim 3 wherein ivermectin is 10 mg/ml, N-methylpyrrolidone is 20% by volume, propylene glycol is 20% by volume, the formulation further comprising 1.5% by volume benzyl alcohol, and water.

* * * * *

UNITED STATES PATENT AND TRADEMARK OFFICE
CERTIFICATE OF CORRECTION

PATENT NO. : 5,773,422    Page 1 of 2

DATED : June 30, 1998

INVENTOR(S) : Komer

It is certified that error appears in the above-identified patent and that said Letters Patent is hereby corrected as shown below:

At columns 1 and 2, please replace the structure with

--

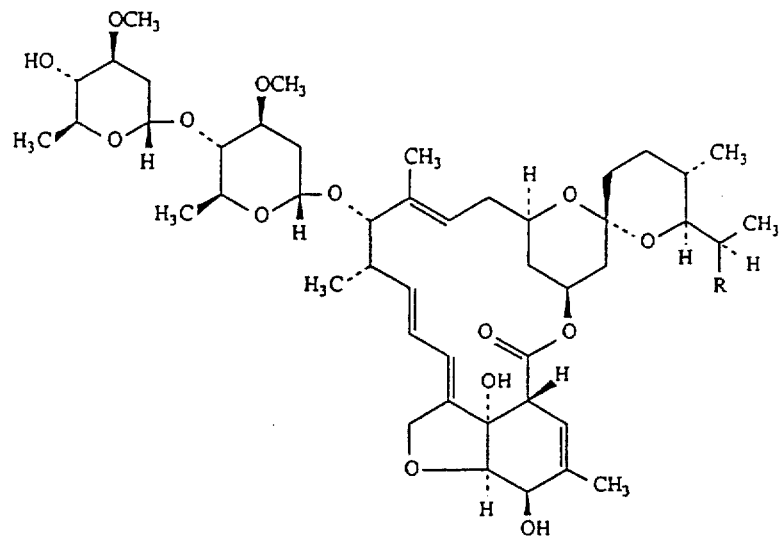

UNITED STATES PATENT AND TRADEMARK OFFICE
CERTIFICATE OF CORRECTION

PATENT NO. : 5,773,422
DATED : June 30, 1998
INVENTOR(S) : Komer

It is certified that error appears in the above-identified patent and that said Letters Patent is hereby corrected as shown below:

component $B_{1a}$, $R = C_2H_5$     component $B_{1b}$, $R = CH_3$

Signed and Sealed this

Sixth Day of October, 1998

Attest:

Attesting Officer

BRUCE LEHMAN

Commissioner of Patents and Trademarks